United States Patent [19]

Albrecht et al.

[11] Patent Number: 5,121,985
[45] Date of Patent: Jun. 16, 1992

[54] OPTICAL MONITOR FOR OBSERVING TURBULENT FLOW

[75] Inventors: Georg F. Albrecht, Livermore, Calif.; Thomas R. Moore, Rochester, N.Y.

[73] Assignee: The United States of America as represented by the United States Department of Energy, Washington, D.C.

[21] Appl. No.: 642,577

[22] Filed: Jan. 17, 1991

[51] Int. Cl.$^5$ .............................. G01N 21/41
[52] U.S. Cl. ................... 356/128; 356/361
[58] Field of Search ............. 356/128, 129, 361, 362

[56] References Cited

U.S. PATENT DOCUMENTS

| | | | |
|---|---|---|---|
| 3,989,938 | 11/1976 | Auth | 235/151 |
| 4,396,943 | 8/1983 | Lord et al. | 358/107 |
| 4,601,579 | 7/1986 | Pritchard et al. | 356/346 |
| 4,732,482 | 3/1988 | Rippel | 356/346 |
| 4,740,082 | 4/1988 | Young | 356/346 |
| 4,796,992 | 1/1989 | Aoshima et al. | 356/347 |
| 4,948,212 | 8/1990 | Cheng et al. | 350/3.64 |
| 5,018,852 | 5/1991 | Cheng et al. | 356/342 |

OTHER PUBLICATIONS

G. F. Albrecht et al., "An Optical Technique for the Measurement of Turbulent Spectra Using the Photorefractive Properties of BaTiO$_3$," UCRL-102551, LLNL.
G. F. Albrecht et al., "Optical technique for the measurement of turbulent spectra using the photorefractive properties of BaTiO$_3$," Appl Phys Lett, vol. 57, No. 9, pp. 864-866, Aug. 27, 1990.
H. F. Robey et al., "An Optical Technique for the Direct Measurement of the 2-D Spectral Density of a Passive Scalar in a Turbulent Flow," LLNL, UCRL-J-C-103552, AAIA 21st Fluid Dynamics, Plasma Dynamics, and Laser Conference, Seattle, Wash., Jun. 18-20, 1990.
H. F. Robey et al., "The Spectrum of a Passive Scalar in the Inertial Convective Subrange of an Anisotropic Turbulent Flow," LLNL, UCRL-JC-103275, Prepared for submittal to Physical Rev Lett, Mar. 1990.
H. Robey et al., "An Optical Technique for the Measurement of Turbulent Spectra Using . . . ," LLNL Viewgraphs.
G. F. Albrecht, "Optical Diagnostics of Gas Flow", UCRL-50021-87, Laser Program Annual Report, LLNL Section 6, pp. 30-33, 1987.
D. Z. Anderson et al., "Optical Filters," IEEE J. of Quantum Electronics, vol. 25, No. 3, pp. 635-647, Mar. 1989.
M. Cronin-Golomb et al., "Photorefractive time differentiation of coherent optical images," Optical Lett, V. 12, N. 12, pp. 1029-1301, 1987.
J. E. Ford et al., "Time-integrating interferometry using photorefractive fanout," Optics Lett, vol. 13, No. 10, pp. 856-858, Oct. 1988.

Primary Examiner—Richard A. Rosenberger
Attorney, Agent, or Firm—Henry P. Sartorio; L. E. Carnahan; William R. Moser

[57] ABSTRACT

The present invention provides an apparatus and method for non-invasively monitoring turbulent fluid flows including anisotropic flows. The present invention uses an optical technique to filter out the rays travelling in a straight line, while transmitting rays with turbulence induced fluctuations in time. The output is two dimensional, and can provide data regarding the spectral intensity distribution, or a view of the turbulence in real time. The optical monitor of the present invention comprises a laser that produces a coherent output beam that is directed through a fluid flow, which phase-modulates the beam. The beam is applied to a temporal filter that filters out the rays in the beam that are straight, while substantially transmitting the fluctuating, turbulence-induced rays. The temporal filter includes a lens and a photorefractive crystal such as BaTiO$_3$ that is positioned in the converging section of the beam near the focal plane. An imaging system is used to observe the filtered beam. The imaging system may take a photograph, or it may include a real time camera that is connected to a computer. The present invention may be used for many purposes including research and design in aeronautics, hydrodynamics, and combustion.

19 Claims, 5 Drawing Sheets

OPTICAL MONITOR FOR OBSERVING TURBULENT FLOW

The United States Government has rights in this invention pursuant to Contract No. W-7405-ENG-48 between the U.S. Department of Energy and the University of California for the operation of Lawrence Livermore National Laboratory.

BACKGROUND OF THE INVENTION

1. Field of the Invention

The present invention relates to non-invasive observation of turbulent flow. More specifically, the present invention relates to transmitting a laser beam through a turbulent flow and temporally filtering the laser beam to provide data that includes useful information regarding the turbulence and the turbulent spectrum of the flow in two dimensions.

2. Description of Related Art

The nature of turbulence is such that great difficulties arise in measurement and observation of turbulent flows and turbulent heat conduction. A turbulent flow may be defined, in a flow of a fluid such as water or air, as a flow in which the local velocities and pressures fluctuate irregularly in a somewhat random manner. Turbulent heat conduction may be defined as the conduction of heat in a fluid by lateral and vertical eddy diffusion, with currents and eddies in a somewhat random manner.

Turbulence affects many events of interest. For example, an airfoil of an aircraft wing may designed to minimize turbulence induced drag, while simultaneously providing lift and maneuverability. The hull of a boat or a submarine may be designed to minimize turbulence. For many uses, including engineering design and real time flow monitoring, observation of turbulent flow is very useful, particularly if the flow can be monitored in real time. Furthermore it is useful if observation occurs non-invasively; i.e., without affecting the properties of the turbulence.

Present theory is incapable of accurately predicting turbulent effects; thus, experimental observation is vital. However, the expense of experimental observation can be large; a full-scale prototype may need to be built. As an example in aeronautics, turbulent effects are not fully appreciated until a prototype aircraft is built and tested in operation-an often expensive and dangerous process. If an accurate method for observing turbulence were available, the aircraft's design could be more fully tested with a low cost model, which would save a great deal of expense and time.

Systems have been developed for monitoring turbulence in a fluid flow. These systems include the standard "hot wire" technique, and Schlieren techniques.

The hot wire technique, which has been known for many years, physically positions a wire in the fluid flow. As fluid flows past the wire, it is cooled according to the local flow conditions. By applying a voltage and monitoring the wire with an ohmmeter, a measure of the amount of cooling can be obtained, which is related to the turbulence. The hot wire technique has many drawbacks, including the fact that the wire itself perturbs the flow; it is an invasive technique. Other drawbacks of the hot wire technique include poor spatial resolution of turbulence, and an aliasing in measurement. The measurements are limited to the one location where the wire is positioned, and do not provide area coverage. Additionally, data evaluation of the hot wire measurements must make assumptions regarding the isotropy of the flow. The most often used assumption of isotropic flow is generally inaccurate; in most situations of interest, the flow is anisotropic.

To address some of these problems, optical techniques have been developed to non-invasively monitor fluid flow. The optical techniques are based upon the phenomenon that the refractive index of a material varies dependent upon the turbulence. This phenomenon is explained by the nature of turbulence, which is a localized compression and decompression, which effects a refractive index change in the material. Thus a light beam passing through the fluid will be deflected (refracted) in an amount dependent upon the turbulence.

It is known that a single, extremely narrow beam may be used to observe turbulence. The deflection of the laser beam may be recorded in real time. However, in order to effectively use the deflection information, a cumbersome deconvolution of the data is required. An additional drawback of the narrow beam method is that it provides information regarding only the narrow line of turbulence through which it passes; the whole picture is unavailable as in the hot wire technique.

To obtain area coverage of turbulent flow, rather than local coverage, it has been suggested to use a larger beam. However, with a larger beam, the deflection information is not available directly. The larger beam includes deflection information from many different rays with different deflections; this information is encoded in the beam in such a manner that it cannot be viewed directly. Furthermore, the intensity of the straight, undeflected rays is typically many orders of magnitude greater than the intensity of the deflected rays which are of interest.

Spatial filter techniques have been used to recover a part of the deflection information. First, the encoded laser beam is focused by a lens. Using Schlieren techniques at the focal plane, the central portion of the beam is physically blocked by a knife edge or a bull's eye. Some of the deflection information is found in the areas surrounding the blocked portion, and thus this information is not blocked. Thus, the spatially filtered beam contains deflection information which can be used to provide a limited measurement of the turbulence in the fluid. The beam may be imaged to provide a "picture" of the turbulence, or the focal plane may be viewed directly to provide information regarding the spectral density of the turbulence.

A significant problem with blocking is the loss of information. Many deflected rays lie within the blocked central region, and this useful information is lost. In fact, the bulk of the turbulent energy has a low wavenumber ($2\pi/\lambda$), and therefore it lies within the blocked central region. Even outside the central block, outlying regions are completely or partially obscured; a knife edge blocks all information over more than one-half of the beam, and a bull's eye has support struts which block a portion of the information of interest. Thus, the physical block greatly reduces the intensity of the desired rays (the "signal"), resulting in a substantial loss of precision and a low signal-to-noise ratio.

None of the prior art systems provide an accurate picture of the turbulent spectrum in two dimensions, and none provide any information about turbulent energies with a low wavenumber. Furthermore, none of the prior art systems can accurately measure an anisotropic fluid flow; i.e., a flow whose spectral density function is different along a first axis than along the axis perpendicular to the first. It would be an advantage to provide an apparatus and method for non-invasively monitoring anisotropic turbulent fluid flow, and providing a two dimensional picture of the turbulent spectrum of that fluid flow, including the portion of the spectrum with low wavenumber.

SUMMARY OF THE INVENTION

The present invention provides an apparatus and method for non-invasively monitoring turbulent fluid flow. The present invention uses an optical technique to filter out the rays travelling in a straight line, while transmitting rays with turbulence induced fluctuations in time. Because an optical block is not used, the output includes the portion of the spectrum with low wavenumber ($2\pi/\lambda$). The output may be used to provide the spectral density of the fluid flow in two dimensions. Alternately, the output may be imaged to view the turbulence in real time. The invention can be used to observe anisotropic fluid flows as well as isotropic fluid flows. The spectral density may be used for heretofore impossible basic research into fluid flow. In addition to basic research, the present invention may be used for many other purposes, for example, airfoil design (aerodynamics) ship design (hydrodynamics), heat flow studies, and combustion research.

The optical monitor of the present invention comprises a laser that produces a coherent output beam. The beam is directed through a fluid flow, through which the beam is phase-modulated by the fluid so that the phase-modulated beam carries information regarding the turbulence in the fluid flow. The beam is applied to a temporal filter that filters out the rays in the beam that are straight for more that a time period $\tau$, which is determined by the characteristics of the temporal filter. This means that the temporal filter substantially passes the fluctuating, turbulence-induced rays that are of interest. The temporal filter includes a lens and a photorefractive crystal such as $BaTiO_3$ that is positioned in the converging section of the beam near the focal plane. The filtered beam may be observed in the focal plane to provide information about the spectral density function. Alternately, the filtered beam may be imaged, so that the turbulence can be viewed with a different perspective, in the time domain.

The laser may be pulsed to provide a single shot that produces a picture of the turbulence at an instant of time. Alternately a series of laser pulses may be applied to give an ensemble average of the turbulence over time. As another alternative, the laser may be operated in cw or quasi-cw operation, and/or the output observed by a television monitor in real time.

An advantage of laser monitoring is that all measurements are made non-invasively. Because turbulent flow is not affected by the measurements, they provide an accurate measurement of the turbulence in the flow of interest. An advantage of the temporal filter is that it passes the bulk of the information of interest, including the low wavenumber information, while substantially attenuating the unwanted beam portions. As a result, the present invention can provide an accurate and useful picture of the spectral density, in two dimensions, with a high signal to noise ratio. The present invention is suitable for monitoring anisotropic flows; that is, those flows that have different types and degrees of turbulence along one axis than the other. Thus, the present invention is suitable for monitoring flow in narrow channels where one dimension is much smaller than the other.

DETAILED DESCRIPTION OF THE INVENTION

The invention is best understood by reference to the figures wherein like parts are designated with like numerals throughout.

Figure 1:
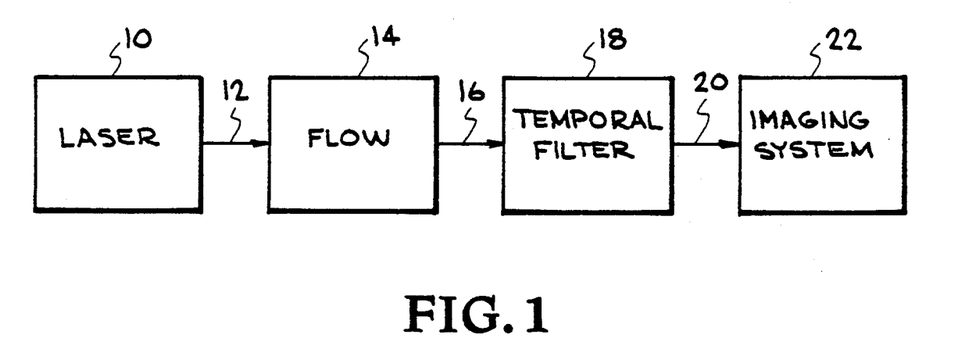
FIG. 1 is a block diagram of the optical monitor of the present invention.

FIG. 1 is a schematic diagram of the present invention, illustrating the general structure of the optical monitor. A laser 10 provides a coherent output beam 12, which is applied to a flow illustrated figuratively by the block 14. Many types of flow 14 may be monitored by the present invention; for example, the flow 14 may comprise a section of the flow of air around an airfoil, or the flow of water through a channel. The present invention has particularly useful application when the flow 14 is turbulent, which causes differences in the index of refraction along at least one axis perpendicular to the direction of propagation. The beam 14, entering the flow 14, is phase-modulated by refractive index differences in the flow 14. A phase-modulated beam 16 exits from the flow 14, and is directed to a temporal filter 18, which selectively filters the beam 16. The temporal filter 18 operates on the phase-modulated beam 16 to output a filtered beam 20 that substantially includes only the temporally fluctuating portion of the phase-modulated beam 16. The filtered beam 20 is then observed by the imaging system illustrated by the block 22, which may include optics and equipment to view the spectral intensity in the Fourier transform plane, or to view a real time image of the turbulence.

Figure 2:
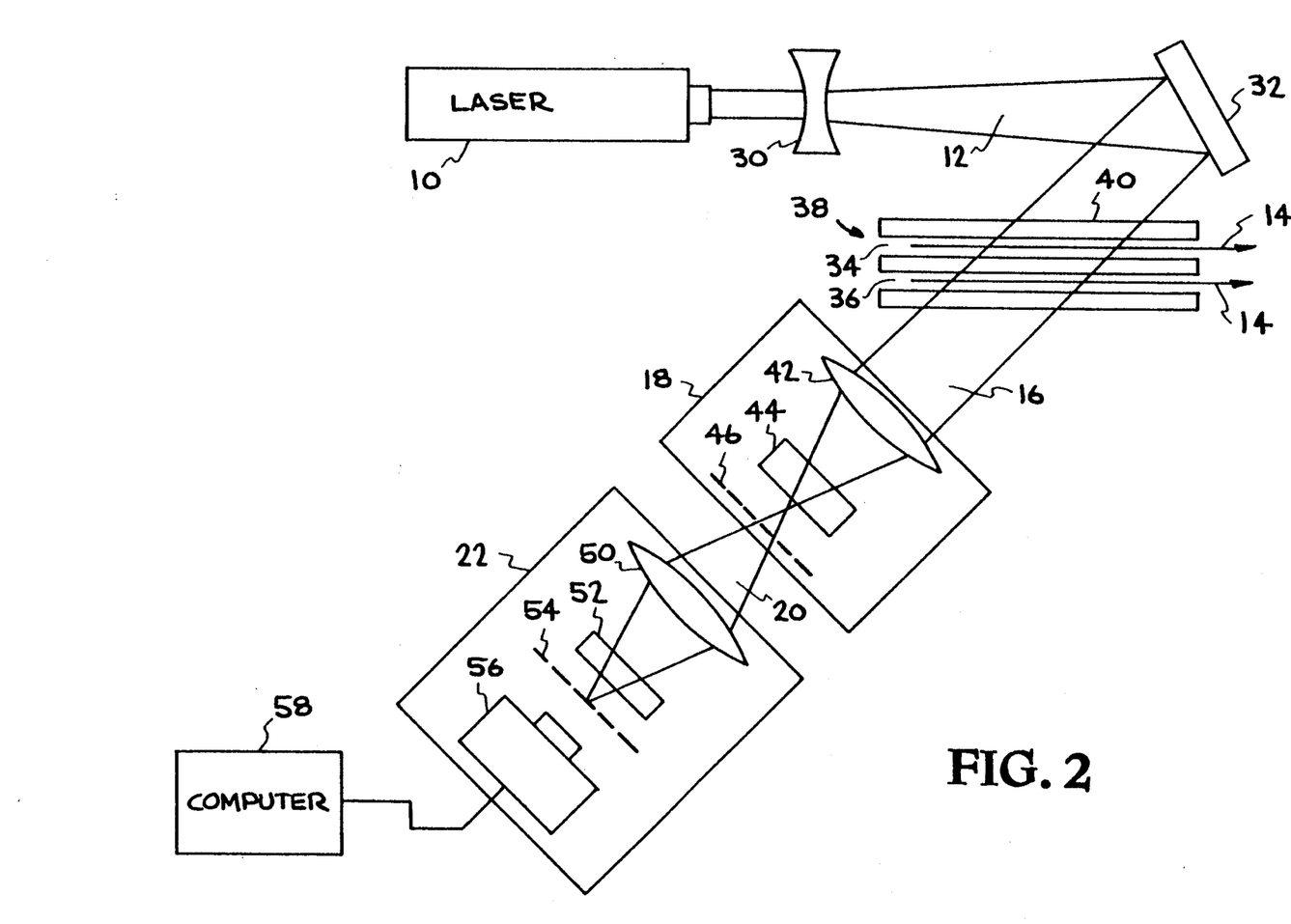
FIG. 2 is a schematic diagram of a preferred embodiment of the optical monitor.

FIG. 2 is a schematic view of a preferred embodiment of the present invention. The laser 10 may comprise a frequency-doubled Nd:YAG laser, producing 100 nanosecond pulses at 1 kHz, although many other types of lasers are suitable. The laser 10 produces a coherent beam 12 which is expanded by a beam expander 30, and directed by a mirror 32 to the flow 14. Many types of flows may be monitored, in FIG. 2, the flow 14 is directed through two channels, a first channel 34, and a second channel 36. A flow structure 38 defining the channels 34,36 comprises a material that is substantially transmissive of the laser beam 12. Preferably, an entrance surface 40 is positioned at Brewster's angle with respect to the incoming beam 12 for effective coupling into the structure 38 and the flow 14.

Figure 3:
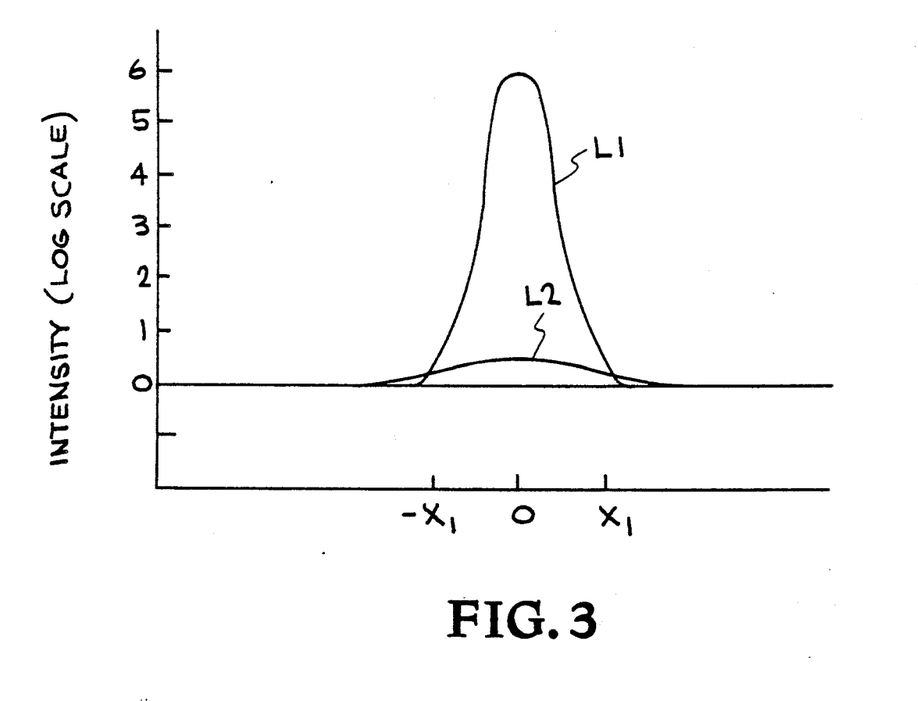
FIG. 3 is a graphical depiction of the intensity of the phase-modulated beam along a cross-section, illustrating the relationship between the straight rays and the phase-modulated rays.

The beam 12 becomes phase-modulated as it passes through the fluid flow 14. In the phase modulation, useful information is imparted to the beam regarding turbulence in the fluid flow 14; however, this useful information has an intensity much less than the rays that pass straight through. FIG. 3 is a graphical illustration, in the focal plane, of the straight rays' intensity (represented by a line L1), and the phase modulated rays' intensity (represented by a line L2) as a function of position in a cross-section of a phase-modulated beam 16. The y scale is a log scale; at the center of the beam (x=0), the intensity of the straight rays may be a million times greater than the intensity of the phase-modulated rays. In the focal plane, the phase-modulated rays' intensity L2 around the center (x=0) includes information regarding the low wavenumber portion of the spectrum. Using a spatial filter block in accordance with prior art methods, the central portion of the beam 16 is physically blocked in the focal plane, for example between $x_1$ and $-x_1$, in order to view the phase-modulated information lying outside that block. However, it can be seen that much phase-modulated information, including the low wavenumber spectrum, is contained in the central region between $x_1$ and $-x_1$; this phase-modulated information is lost using the prior art spatial filter method.

The present invention applies the temporal filter 18 to substantially attenuate the straight rays' intensity L1, while substantially passing the phase-modulated intensity L2, thereby permitting observation of the phase modulation in the central portion of the beam 16 as well as the outer portion of the beam 16. The temporal filter 18 comprises a focusing lens 42 and a photorefractive crystal 44 positioned in a converging section of the beam near the focal plane 46. The photorefractive crystal preferably comprises $BaTiO_3$, and is positioned a few millimeters from the focal plane 46. The width of the photorefractive crystal 44 is preferably small, for example several millimeters, because the interaction length of the beam within the photorefractive crystal 44 must be less than the coherence length of the laser 10, which may be a centimeter or less. The optical properties of the photorefractive crystal 44 are derived from stimulated photorefractive scattering (SPS), which has been investigated in recent years. The photorefractive crystal has a certain response time $\tau$ with which it responds to externally applied optical fields. Temporal variations of the optical field which are slower than $\tau$ are scattered out of the beam by SPS or multiple beam coupling, allowing transmission of only the fluctuating, incoherent field whose time scale t is much less than $\tau$. The crystal response time, $\tau$, depends on the crystal 44 itself, and on the intensity of the laser beam. The crystal response time, $\tau$, can be varied from milliseconds to hours by, for example, adjusting the laser power and/or placing the crystal 44 at different positions relative to the focal plane 46. Thus, a means is provided for discrimination against slowly varying time scales such as are caused, for example, by room air convection. In effect, the temporal filter 18 acts like a high-pass filter.

The phase-modulated beam 16 that entered the temporal filter 18 exits as a filtered beam 20 that can be observed directly to provide useful information. In FIG. 2, the filtered beam 20 can be viewed with the conventional imaging system 22, which includes an imaging lens 50, a neutral density filter 52, a diffuser screen 54, and a camera 56. The diffuser screen 54 provides an image to the camera 56, which is focused on it.

The neutral density filter 52 is selected with a value to attenuate the laser beam 20 so that it can be viewed with the camera 56 with a desired exposure. The camera 56 may be a photographic camera, which takes still photograph, or it may be a real time (video or CCD) camera. In the latter case when a real time camera 56 is used, it may be advantageous to connect a conventional computer 58 to the camera 56 in order to provide image acquisition, digital analysis, or other functions that can be performed by the computer 58.

Lens 50 can be positioned to image the focal plane on the diffuser screen 54, in which case the camera 56 views the spectral density of the beam in two dimensions transverse to the direction of beam propagation. For many applications, the spectral density provides much useful information. In an alternate configuration, the lens 50 may be positioned to provide an image of the flow 14 on the diffuser screen 54 in order to provide an image of the refractive index differences in the fluid flow 14.

In operation, the laser 10 may produce a pulse which is applied to the flow 14, the temporal filter 18, and the imaging system 22 with the proper exposure to provide a picture of the turbulence during the pulse. Alternately, a series of laser pulses may be applied to give an ensemble average of the turbulence over time. As another alternative, the laser may be operated in cw or quasi-cw operation, and the output observed by a television monitor or a computer data processing system in real time.

The experimental arrangement used to obtain spectra can be explained with reference to FIG. 2. The beam from the Quantronix model 114 frequency-doubled Nd:YAG laser 10 operating at 532 nm with very nearly diffraction-limited beam quality is expanded with the 30 cm negative lens 30 and propagated through a section of heated turbulent channel flow 14 confined by optical quality windows 38 with an entrance 40 at the Brewster angle. The Q-switched pulse length of $\leq 100$ ns was short enough to effectively freeze the motion of the flow 14. The rep rate of the laser 10 was 1 kHz which allowed for the ensemble averaging of the photographs produced by the camera 56. The phase-modulated beam 16 is focused by a 15 cm lens through the $BaTiO_3$ crystal 44 located $\sim 2$ mm in front of the focal plane 46 to enhance SPS. The extinction of the coherent part of the beam was measured in the absence of flow and heat addition and was found to be $\sim 10^3$ for one crystal 44 and $10^5$ when two crystals 44 in series were used. The focal spot is then magnified and reimaged onto the diffuser screen 54 from which it is photographed by the camera 56 on Kodak p3200 film. The far field was recorded with different exposure times and with the insertion of various neutral density filters 52 to enhance or suppress various portions of the wave number spectrum.

The particular flow 14 under study consisted to two 4-mm wide channels 34,36 on either side of a center plate which was heated on each side with an indium-tin-oxide film producing a surface heat flux of up to 5 $W/cm^2$. The flow 14 in each channel 34,36 was a fully developed turbulent channel flow of $N_2$ at 2 atm. The Reynolds number based on the channel width D was 16,300, the center line velocity was 35 m/s, and the area examined was a circular area of diameter 4 mm located $\sim 20$ cm or 50 channel widths from the channel entrance nozzle.

Figure 4:
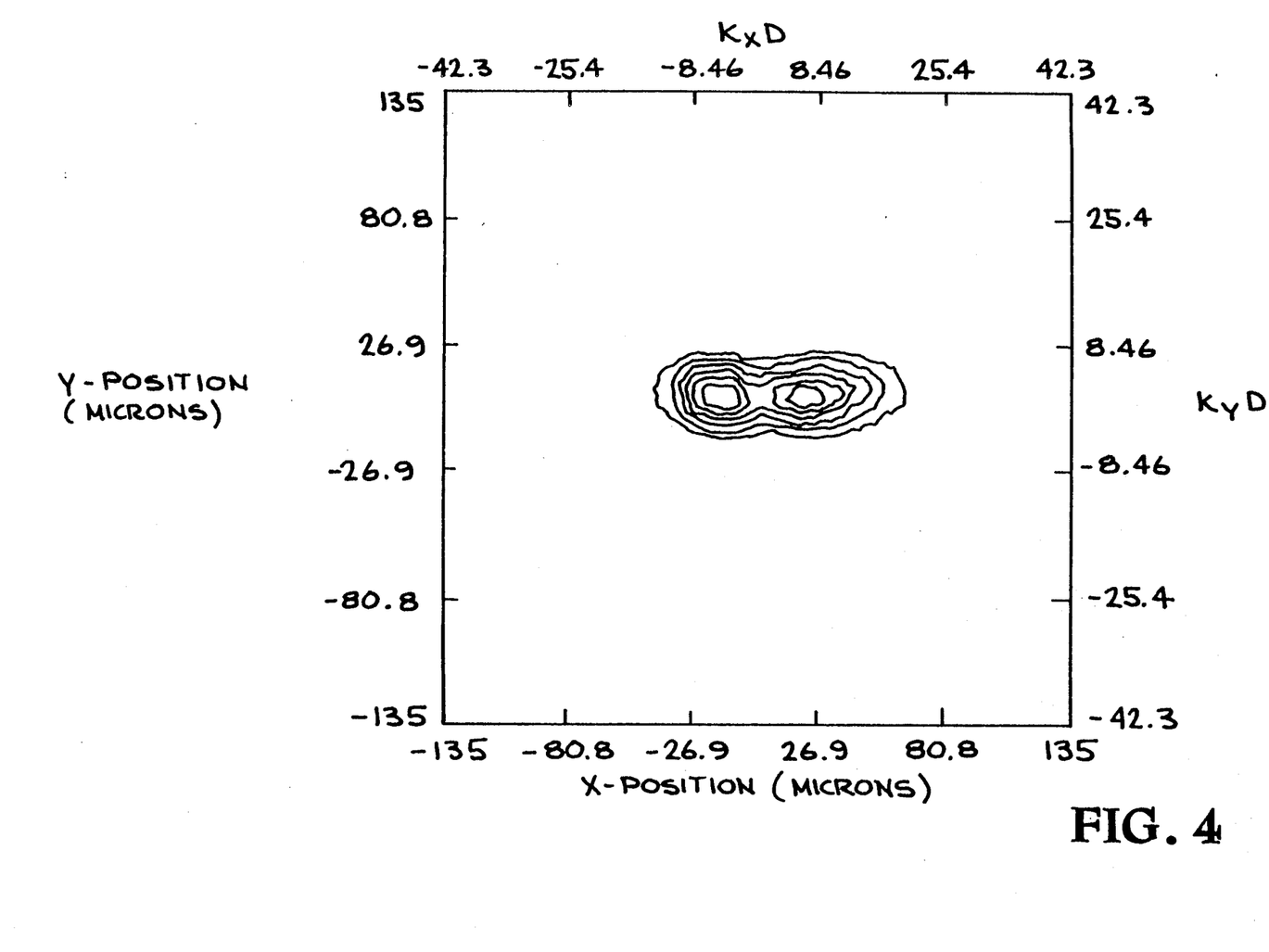
FIG. 4 is a computer-enhanced photograph of the intensity distribution at the focal plane in an experiment with a $\frac{1}{8}$ second exposure.
Figure 5:
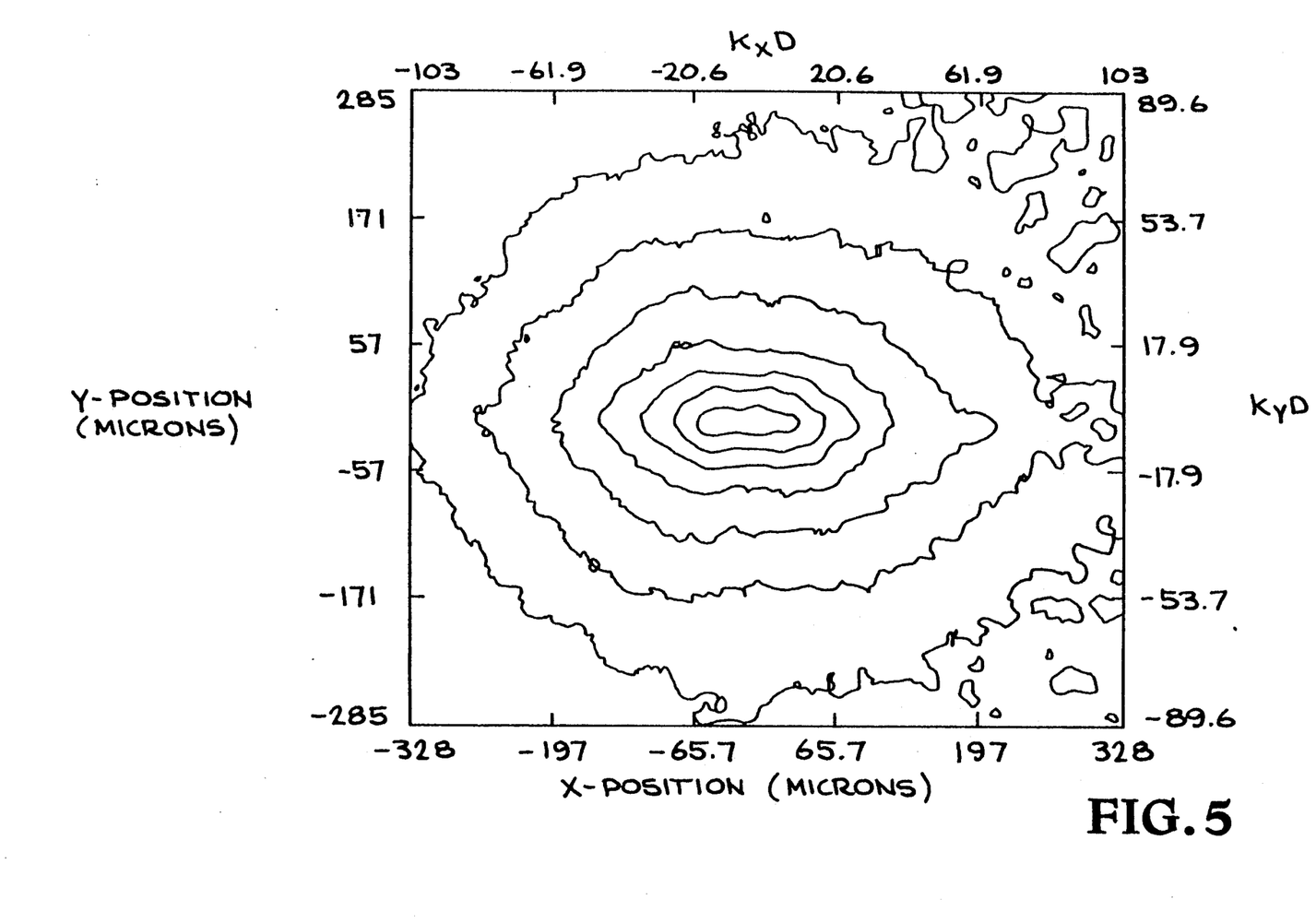
FIG. 5 is a computer-enhanced photograph of the intensity distribution at the focal plane in an experiment with a 16 second exposure.

FIGS. 4 and 5 are representative photographs of the intensity distribution at the focal plane 54 in experiments of the present invention. The photographs of the focal plane exposure distribution were digitized with a microdensitometer and calibrated to give the relative intensity. The resolution in the focal plane is less than 1 $\mu$m in both x and y. FIG. 4 shows a photograph of the recorded intensity obtained with a surface heat flux of 4 W/cm$^2$ and an exposure time of $\frac{1}{8}$ second. The axes give the actual spatial dimensions in the focal plane as well as the normalized wave numbers, $k_xD$ and $k_yD$, where D is the channel width. The flow 14 (FIGS. 1 and 2) is in the x direction. The short exposure time in FIG. 4 enhances the visualization of the lowest wave number part of the spectrum as that part of the spectrum contains the bulk of the turbulent energy and therefore generates the largest contribution to the scattered spectrum. The low wave number spectrum appears in the central region of the photograph in FIG. 4. The two well defined peaks at $k_yD \approx \pm 6$ correspond to flow structures with a dominant spatial wavelength equal to the channel width. Note that the scattered intensity decreases for wave numbers smaller than this. The flow at this scale is clearly anisotropic with the scattered spectrum being at least three times wider in the y direction than in the flow direction. This corresponds to turbulent eddies which are aligned with the flow 14 in the x direction and are three times longer in the flow direction than in the transverse direction.

FIG. 5 is a photograph that shows a longer time exposure of 16 seconds which brings out the higher wave number part of the spectrum (the regions further away from the center). The highest wave numbers in this plot correspond to turbulent flow structures which are nearly 20 times smaller than the channel thickness D or structures measuring ~20 $\mu$m. Note that 20 $\mu$m is still far from the ultimate resolution limit of the technique, which is believed to be given by the diffraction limit of the system and depends on the f/number of the collecting lens and the laser wavelength ($\approx 3$ $\mu$m in the present setup).

The present invention provides a simple method for acquiring two-dimensional, time-resolved spectra of turbulent flows 14. The method is nonintrusive, simple to implement, and applicable to a wide class of flows 14. Using a camera 56 with a sensitive solid-state imaging array instead of film, and conventional computer hardware 58, the time to acquire and process a two-dimensional spectrum could be reduced from the experimental time of more than one day (film development, digitization, calibration, etc.) to a fraction of a second, allowing for the acquisition of spectra in nearly real time. This would allow for the study of nonstationary flows whose spectra evolve with time as well as facilitating the possibility of real time feedback control of turbulent flows. Furthermore, real time data processing could display the results in other forms, like the turbulent energy versus wave number.

Figure 6:
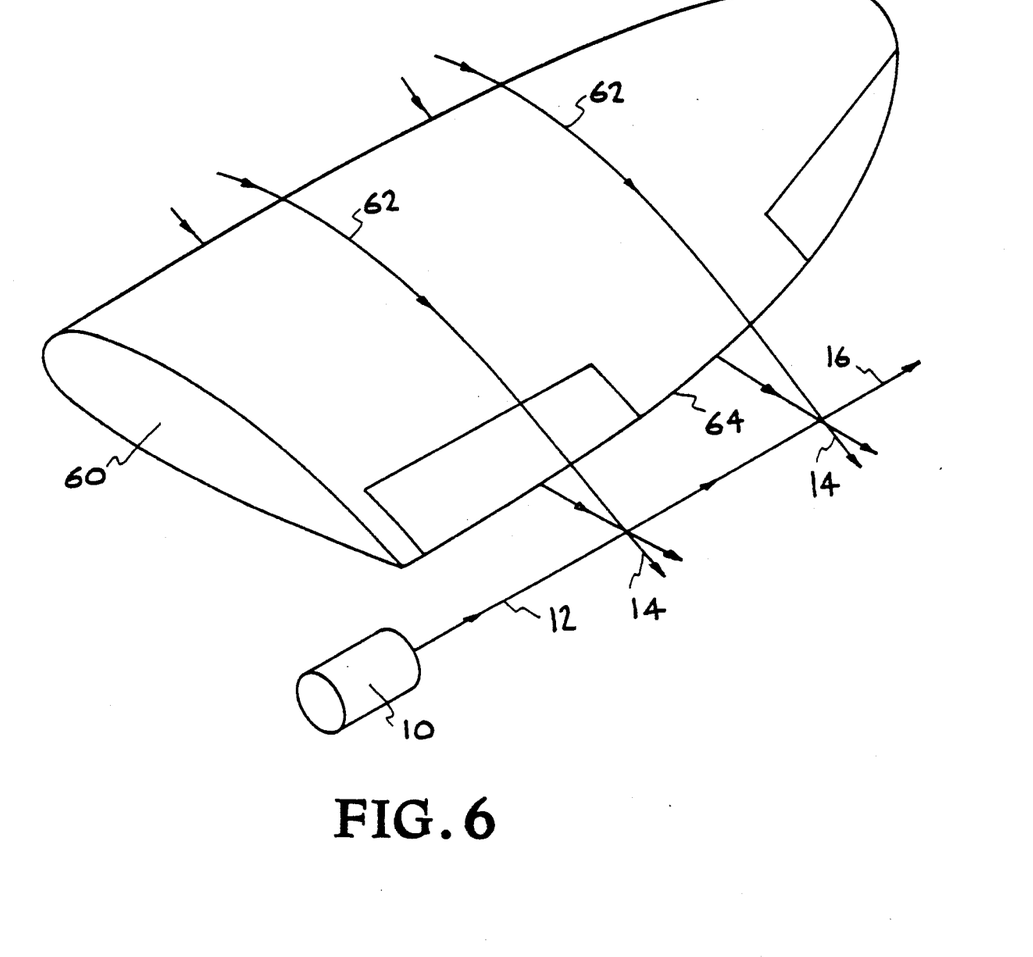
FIG. 6 is an example of an application of the present invention to monitoring turbulence off the trailing edge of an airfoil.

FIG. 6 illustrates one application of the monitor of the present invention. An airfoil 60 is placed in a conventional wind tunnel, creating an airflow 62 around the airfoil 60. The turbulence in the airflow 62 can be measured anywhere, but there may be particular interest in the turbulenece that is created in the flow 62 off the trailing edge 64. The laser beam 12 from the laser 10 (FIG. 1) may be applied through this flow 14 at that point to produce a phase-modulated beam 16 that is then processed in accordance with the above description in order to provide information regarding turbulence.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing descriptions. All changes which come within the meaning and range of equivalency of the claims are to be embraced within their scope.

We claim:

1. An optical monitor for observing the flow of a fluid, said monitor comprising:
   means for producing a coherent laser beam;
   means for directing the laser beam through the fluid flow so that a phase modulated beam is produced;
   a temporal filter whose input is the phase modulated beam, and whose output is a filtered beam; and,
   means for viewing the filtered beam.

2. The optical monitor as claimed in claim 1, wherein the temporal filter comprises a lens and a photorefractive crystal positioned near the focal plane of the lens.

3. The optical monitor as claimed in claim 2, wherein the photorefractive crystal comprises BaTiO$_3$.

4. The optical monitor as claimed in claim 1, wherein the viewing means comprises a camera.

5. The optical monitor as claimed in claim 4, wherein the camera is positioned to view the focal plane of the filtered beam.

6. The optical monitor as claimed in claim 4, wherein the viewing means comprises a photographic camera.

7. The optical monitor as claimed in claim 4, wherein the viewing means comprises a real time camera.

8. The optical monitor as claimed in claim 7, wherein the real time camera is connected to a computer.

9. An optical monitor for observing the flow of a fluid, said monitor comprising:
   a laser that produces a substantially coherent laser beam;
   means for directing the laser beam through the fluid flow to produce a phase modulated beam;
   a temporal filter positioned to filter the phase-modulated beam, said temporal filter having a time constant $\tau$, said temporal filter substantially transmitting portions of the beam that fluctuate with a time less than $\tau$, while substantially attenuating portions of the beam that have a time greater than $\tau$; and,
   an imaging system positioned for viewing the filtered beam.

10. The optical monitor as claimed in claim 9, wherein the temporal filter comprises a lens and a photorefractive crystal positioned in the converging section of the beam near the focal plane of the lens.

11. The optical monitor as claimed in claim 10, wherein the photorefractive crystal comprises BaTiO$_3$.

12. The optical monitor as claimed in claim 9, wherein the imaging system comprises a camera.

13. The optical monitor as claimed in claim 12, wherein the imaging system comprises a computer that is connected to the camera.

14. A method of monitoring the flow of a fluid using a temporal filter with a time constant $\tau$, said method comprising:
   (a) providing a coherent laser beam;
   (b) applying the coherent laser beam to the fluid flow to produce a phase-modulated beam;

(c) applying the phase-modulated beam to a temporal filter that substantially attenuates those rays that are constant for a time greater than the time constant $\tau$, to provide a filtered beam that includes substantially only the portion of the phase-modulated beam that fluctuates in a time less that $\tau$; and, (d) observing the filtered beam.

15. The monitoring method as claimed in claim 14, wherein, in the step (d), the filtered beam is focused by a lens and observed in a focal plane of the lens, whereby the spectral intensity distribution is observed.

16. The monitoring method as claimed in claim 14, wherein, in the step (a), the laser beam comprises a series of pulses that are observed in the step (d) to provide an ensemble average of the fluid flow.

17. The monitoring method as claimed in claim 16, wherein, in the step (d), a single photograph is formed of the series of laser pulses.

18. The monitoring method as claimed in claim 14, wherein the step (d) comprises observing the filtered beam with a camera in real time.

19. The monitoring method as claimed in claim 18, further comprising a step (e), wherein the camera provides an output to a computer.

* * * * *